(12) United States Patent
Meskens et al.

(10) Patent No.: US 8,175,306 B2
(45) Date of Patent: May 8, 2012

(54) WIRELESS COMMUNICATION BETWEEN DEVICES OF A HEARING PROSTHESIS

(75) Inventors: Werner Meskens, Opwijk (BE); Koen Van den Heuvel, Hove (BE)

(73) Assignee: Cochlear Limited, Macquarie University, NSW (AU)

( * ) Notice: Subject to any disclaimer, the term of this patent is extended or adjusted under 35 U.S.C. 154(b) by 770 days.

(21) Appl. No.: 12/168,498

(22) Filed: Jul. 7, 2008

(65) Prior Publication Data

US 2009/0067653 A1 Mar. 12, 2009

Related U.S. Application Data

(60) Provisional application No. 60/948,415, filed on Jul. 6, 2007.

(51) Int. Cl.
*H04R 25/00* (2006.01)

(52) U.S. Cl. ....... 381/315; 381/23.1; 381/316; 381/328; 381/330

(58) Field of Classification Search .................. 381/23.1, 381/312–316, 323, 328–331; 602/25; 607/55, 607/57

See application file for complete search history.

(56) References Cited

U.S. PATENT DOCUMENTS

| | | | |
|---|---|---|---|
| 7,218,900 B2 * | 5/2007 | Suzuki | 455/180.1 |
| 7,515,935 B2 * | 4/2009 | Ibrahim et al. | 455/553.1 |
| 7,738,913 B2 * | 6/2010 | Hilpisch et al. | 455/550.1 |
| 2005/0289224 A1 * | 12/2005 | Deslippe et al. | 709/208 |
| 2006/0012476 A1 * | 1/2006 | Markhovsky et al. | 340/539.32 |
| 2006/0039577 A1 * | 2/2006 | Sanguino et al. | 381/315 |
| 2006/0274747 A1 * | 12/2006 | Duchscher et al. | 370/389 |
| 2007/0009124 A1 * | 1/2007 | Larsen | 381/315 |
| 2007/0036280 A1 * | 2/2007 | Roeck et al. | 379/52 |
| 2007/0086601 A1 * | 4/2007 | Mitchler | 381/79 |
| 2007/0201412 A1 * | 8/2007 | Ji et al. | 370/338 |
| 2008/0039902 A1 * | 2/2008 | Hartley et al. | 607/57 |
| 2008/0144493 A1 * | 6/2008 | Yeh | 370/230 |
| 2008/0175421 A1 * | 7/2008 | Chizari | 381/315 |
| 2009/0180651 A1 * | 7/2009 | Hilpisch et al. | 381/315 |
| 2009/0216296 A1 * | 8/2009 | Meskens | 607/57 |
| 2009/0245551 A1 * | 10/2009 | Nielsen | 381/315 |
| 2011/0058699 A1 * | 3/2011 | Kilsgaard | 381/315 |

FOREIGN PATENT DOCUMENTS

| | | |
|---|---|---|
| EP | 1231819 | 8/2002 |
| WO | WO2004/110099 | 12/2004 |

OTHER PUBLICATIONS

Partial European Search Report, European Application No. EP 08012327.6, mailed Jul. 26, 2011 (6 pages).

* cited by examiner

*Primary Examiner* — Eugene Lee
*Assistant Examiner* — Mohammed Shamsuzzaman
(74) *Attorney, Agent, or Firm* — Kilpatrick, Townsend & Stockton, LLP.

(57) ABSTRACT

A method of wireless communication between hearing aid devices of a hearing prosthesis. A first device selects a frequency channel for bidirectional wireless communication from a predefined series of frequency channels. A second device transmits a command signal repeatedly over the series of frequency channels until it transmits the command signal over the frequency channel selected by the first device. Subsequent commands send by the second device to the first device are initially transmitted over the selected frequency channel.

22 Claims, 8 Drawing Sheets

FIG. 7

WIRELESS COMMUNICATION BETWEEN DEVICES OF A HEARING PROSTHESIS

CROSS-REFERENCE TO RELATED APPLICATIONS

The present application claims the benefit of U.S. Provisional Patent Application 60/948,415, filed Jul. 6, 2007, which is hereby incorporated by reference herein.

BACKGROUND

1. Field of the Invention

The present invention relates generally to hearing prostheses and, more particularly, to wireless communications between devices of a hearing prosthesis.

2. Related Art

Hearing prostheses typically include devices which are non-implantable as well as devices which are fully- or partially implantable. A partially implantable hearing prosthesis typically comprises an implantable device that delivers direct or indirect mechanical or electrical stimulation to the inner or middle ear of the recipient. Such hearing prostheses also include one or more external devices which process auditory signals and which transfer a representation of the auditory signals to the implanted device. Such external devices typically include a microphone that converts auditory signals into an electrical signal, and a sound processor that processes the electrical signal to generate an encoded output signal. The encoded output signal is then wirelessly transcutaneously transmitted to the implantable device.

If the hearing prosthesis is a Cochlear™ implant (commonly referred to as a Cochlear™ device, Cochlear™ implant device, Cochlear™ implant system, and the like; hereinafter "cochlear implant"), the encoded signals are delivered to an implantable device commonly referred to as a receiver/stimulator unit. The stimulator unit generates electrical stimulation signals which are delivered to the auditory nerves by means of an electrode carrier member implanted in the recipient's cochlea. This allows the recipient's brain to perceive a hearing sensation resembling the natural hearing sensation normally delivered by the auditory nerve. When the auditory nerve is absent or inoperative, brainstem stimulation may be applied.

External electronic components comprising auditory transducers, signal processors and memory, user interfaces and batteries support the implantable components of the hearing prosthesis. Some of these external devices are miniaturized and worn behind the ear of the recipient. Oftentimes, a behind-the-ear (BTE) or sound processor unit houses one or more of such external devices.

Since hearing prostheses contain active components, they are provided with a battery. For example, the behind-the-ear unit noted above typically has an attached headpiece housing a coil for transferring power to the implanted devices via magnetic induction. It is known to provide the behind-the-ear device with a slot or compartment for a power supply module. Power supply modules with different types of batteries are provided to be inserted into that compartment. By way of example, the power supply module may comprise a carrier for replaceable Zn-Air batteries or a fixed rechargeable battery. This arrangement enables the batteries to be readily replaced.

Some hearing prostheses include remote units which are operably coupled to the BTE devices. Such remote units may include user interfaces which allow the recipient and/or audiologist, clinician or other health care provider (audiologist herein) to customize the cochlear implant, as well as to gain feedback concerning the operating status of the hearing prosthesis, to adjust the volume or sensitivity of the sound processor, to select which speech program is to be used, etc. A remote unit may also comprise a human interface. A remote unit with larger control buttons for controlling the implant, a clearly displayed status indication and connectivity to a personal computer are additional benefits. The remote unit may communicate wirelessly with the BTE device. For example, the remote unit may be provided with a RF signal transmitter and/or receiver and with a RF antenna. Wireless hearing prostheses enlarge possibilities and improve ease of use for the recipient and audiologist.

SUMMARY

In accordance with one aspect of the present invention, there is disclosed a hearing prosthesis comprising a first device and a second device arranged for receiving commands from the first device, wherein: the first and the second devices each comprise a transmitter and receiver arranged for communication over a wireless communication link, the second device being configured to select a frequency channel for bidirectional wireless communication from a predefined series of frequency channels, the first device being configured to transmit a command signal repeatedly over a plurality of frequency channels which includes the frequency channel selected by the second device, and the first device being configured to initiate transmission of a subsequent command over the frequency channel selected by the second device.

According to another aspect of the present invention, there is disclosed a method of wireless communication between a first device and a second device of a hearing prosthesis, the method comprising: selecting, by the second device, a frequency channel for bidirectional wireless communication from a predefined series of frequency channels, preparing by the first device a command for the second device, sending the command from the first device repeatedly over a plurality of frequency channels, the plurality of frequency channels including the frequency channel selected by the second device, until a reply signal is received by the first device, and using the frequency channel selected by the second device as the initial frequency channel for transmitting a subsequent command sent by the first device to the second device.

According to a further aspect of the present invention, there is disclosed a method of wireless communication between multiple devices of a hearing prosthesis having first, second and third devices, comprising: transmitting a signal from the first device to the second device, receiving the signal by the second device, optionally modifying the signal in a first predetermined manner and transmitting the signal, unmodified or modified, from the second device to the third device, receiving the signal by the third device, optionally modifying the signal in a second predetermined manner and transmitting the signal, unmodified or modified, from the third device to the first device and receiving the signal by the first device and comparing the signal that is received with the signal that was transmitted.

BRIEF DESCRIPTION OF THE DRAWINGS

Embodiments of the present invention are described below with reference to the following figures in which.

DETAILED DESCRIPTION

Embodiments of the present invention are generally directed toward wireless communicating between devices of a hearing prosthesis. A first device selects a frequency channel for bidirectional wireless communication from a predefined series of frequency channels. A second device transmits a command signal repeatedly over the series of frequency channels until it transmits the command signal over the frequency channel selected by the first device. Subsequent commands sent by the second device to the first device are initially transmitted over the selected frequency channel.

Figure 1:
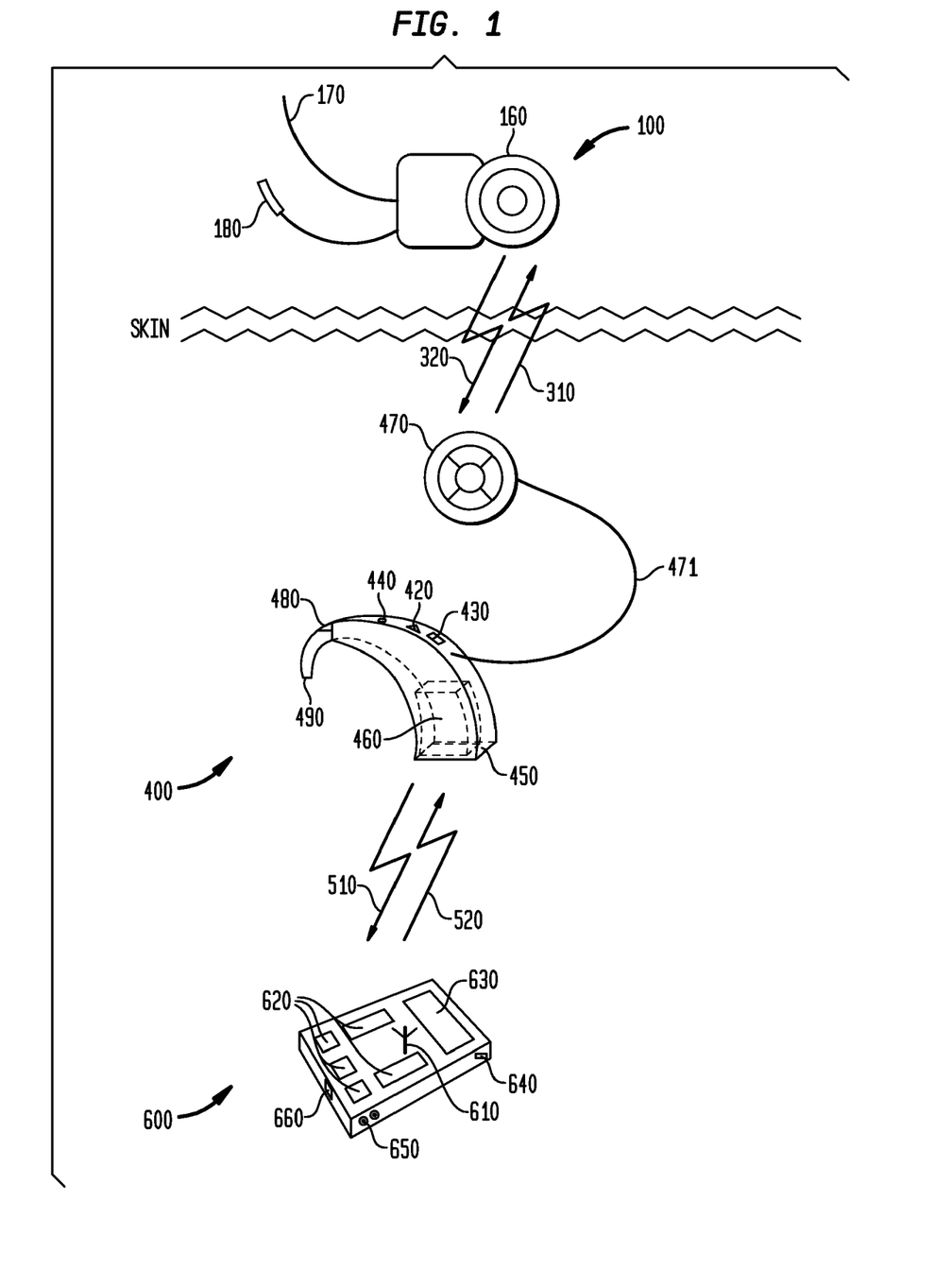
FIG. 1 is a perspective view of a partially implantable hearing prosthesis in accordance with one embodiment of the present invention.

A perspective view of a partially implantable hearing prosthesis is shown in FIG. 1. The hearing prosthesis comprises three different primary devices: a behind-the-ear device 400, an implantable device 100 and a remote unit 600. The hearing prosthesis converts airborne sound waves captured by a microphone into stimuli signals applied to the middle ear, inner ear or brainstem by means of an electrode or actuator.

Implantable device 100 is an active electronic medical device typically implanted under the human skin near the left or right ear. In this illustrative embodiment, implantable device 100 comprises an implantable electrode 170 that stimulates by delivering electrical signals to the auditory nerves of the cochlea and/or the brainstem. Depending on the cause of the recipient's deafness, implantable device 100 may alternatively or additionally include a mechanical implantable actuator 180 that stimulates the middle or inner ear.

In one embodiment, the main assembly of behind-the-ear device 400 comprises a main housing, a carrier for plug-in modules such as battery packs 460, an ear hook 490 and a headpiece 470. In certain embodiments, the housing is formed of metallic material, ceramic material, polymeric material or a combination of such materials. Implantable device 100 further comprises a microphone 440, a human user interface with control buttons 420 and small display 430, digital and analog interface 450, a signal processor with memory and a battery slot for a replaceable part 460 such as a carrier 462 for Zn-Air batteries or a rechargeable Lithium-ion battery pack 461.

BTE device 400 is configured to accept a removable connection to a headpiece 470 via a cable 471. Headpiece 470 comprises an antenna coil or closed wire loop that is capable of transmitting and receiving signals to/from a complementary antenna 160 of implantable device 100. Such forward 310 and backward 320 telemetry links between BTE device 400 and implantable hearing aid device 100 are based on magnetic induction coupling, utilizing the non-propagating quasi-static magnetic field. The magnetic field may have a very high roll-off behaviour as a function of distance. Forward link 310 additionally may supply power to the implantable device 100.

BTE device 400 is additionally configured to receive and transmit telemetry signals over a wireless electromagnetic RF link 510 and 520, based on electromagnetic field propagation. The power for a plane wave in the far field rolls-off as one over the distance from the source squared. This second type of communication link enables a larger wireless communication range. Therefore BTE device 400 may use an appropriate monopole, dipole or any other suitable antenna 480. Antenna 480 may advantageously be integrated in ear hook 490. This is illustrated in FIG. 3, described in greater detail below.

Wires 482 (FIG. 3) provide coupling of antenna 480 to the printed circuit board (PCB) of the BTE device. This latter placement of antenna 480 has the advantage that no additional space is required for the antenna and its location is advantageously on the subject of RF emission efficiency at higher frequencies, e.g. the 2.4 GHz unlicensed frequency band. Alternative locations for antenna placement may be implemented in alternative embodiments of the present invention. For example, in one embodiment, the antenna is placed within a removable power supply (battery) module 465.

The extended range of operation obtainable with this type of coil-less link 510, 520 may be beneficial for parents wanting to verify or even control their child's hearing aid system, which may be a partially implanted system. This verification or control may be performed through a remote unit 600 which communicates with BTE device 400 via wireless link 510 and 520. The RF link 510, 520 allows operating the remote unit a comfortable distance away from BTE device 400. Remote unit 600 may report on the status of the partially implanted system (battery level, operating status of the link between BTE and cochlear implant, etc.).

Figure 3:
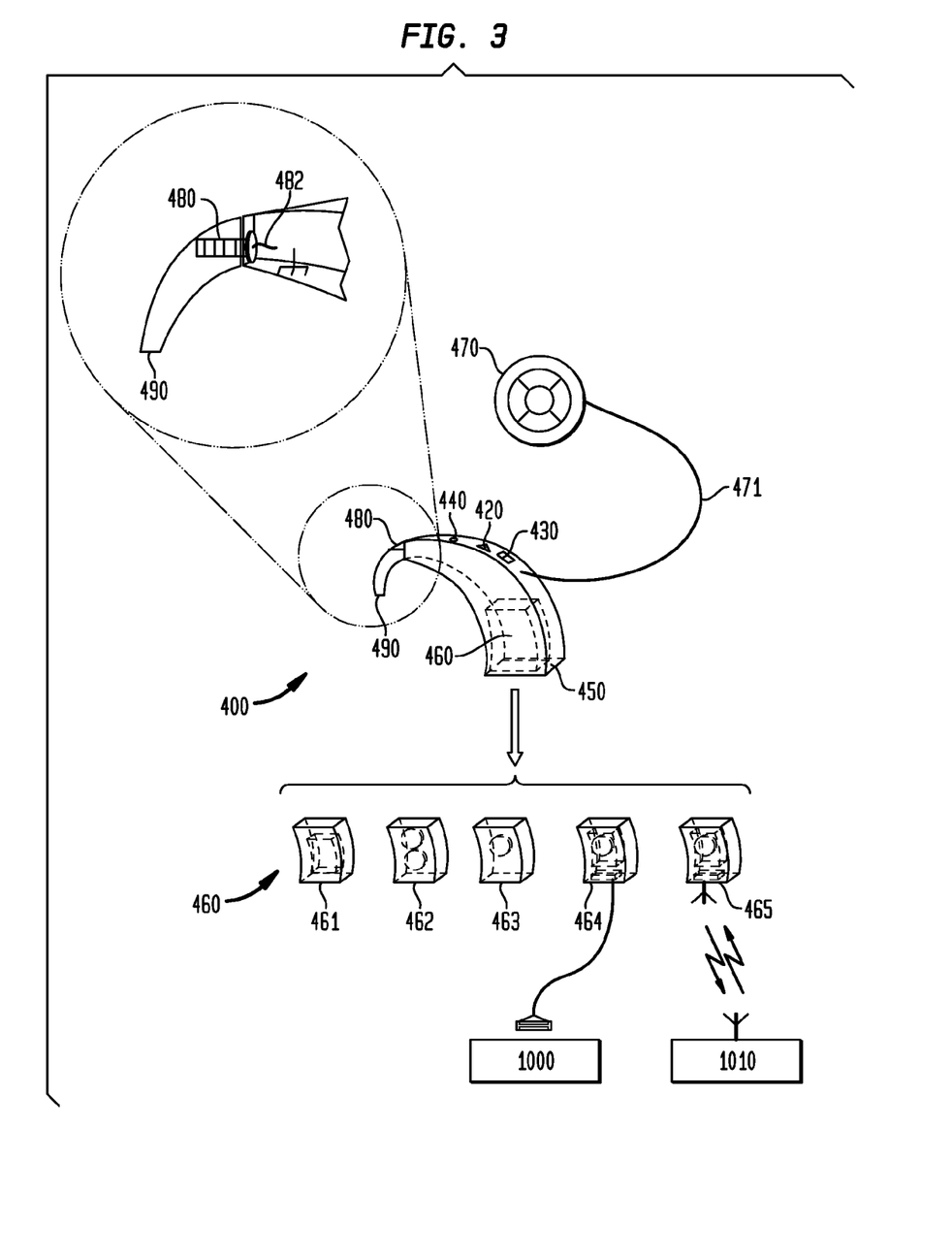
FIG. 3 is a perspective view of a BTE device with an RF antenna and a replaceable power supply, in accordance with one embodiment of the present invention.

FIG. 3 is a perspective view of one embodiment of behind-the-ear device 400. This embodiment of behind-the-ear device 400 comprises a compartment 460 for plug-in modules. The illustrated plug-in modules may be a battery carrier 463 for one Zn-Air battery or a carrier 462 for two Zn-Air batteries, a rechargeable battery module 461, or any combination of preceding modules. The plug-in module may comprise an integrated wired interface 464, or wireless interface 465 enabling remote connectivity with peripheral data devices 1000 or 1010, respectively.

Returning to FIG. 1, the figure depicts one embodiment of remote unit 600 that is dimensioned to be a handheld device. Remote unit 600 comprises a receiver and transmitter system with antenna 610 for bidirectional wireless communication with BTE device 400, using links 510 and 520. Links 510 and 520 may, in certain embodiments, be based on electromagnetic field propagation. According to one embodiment of the invention, wireless link 510, 520 is an electromagnetic RF link. Remote unit 600 also comprises a microphone system 640, a human user interface with control buttons 620 and display 630, digital and analog inputs and outputs 650, a microcontroller, memory and replaceable batteries.

Figure 4:
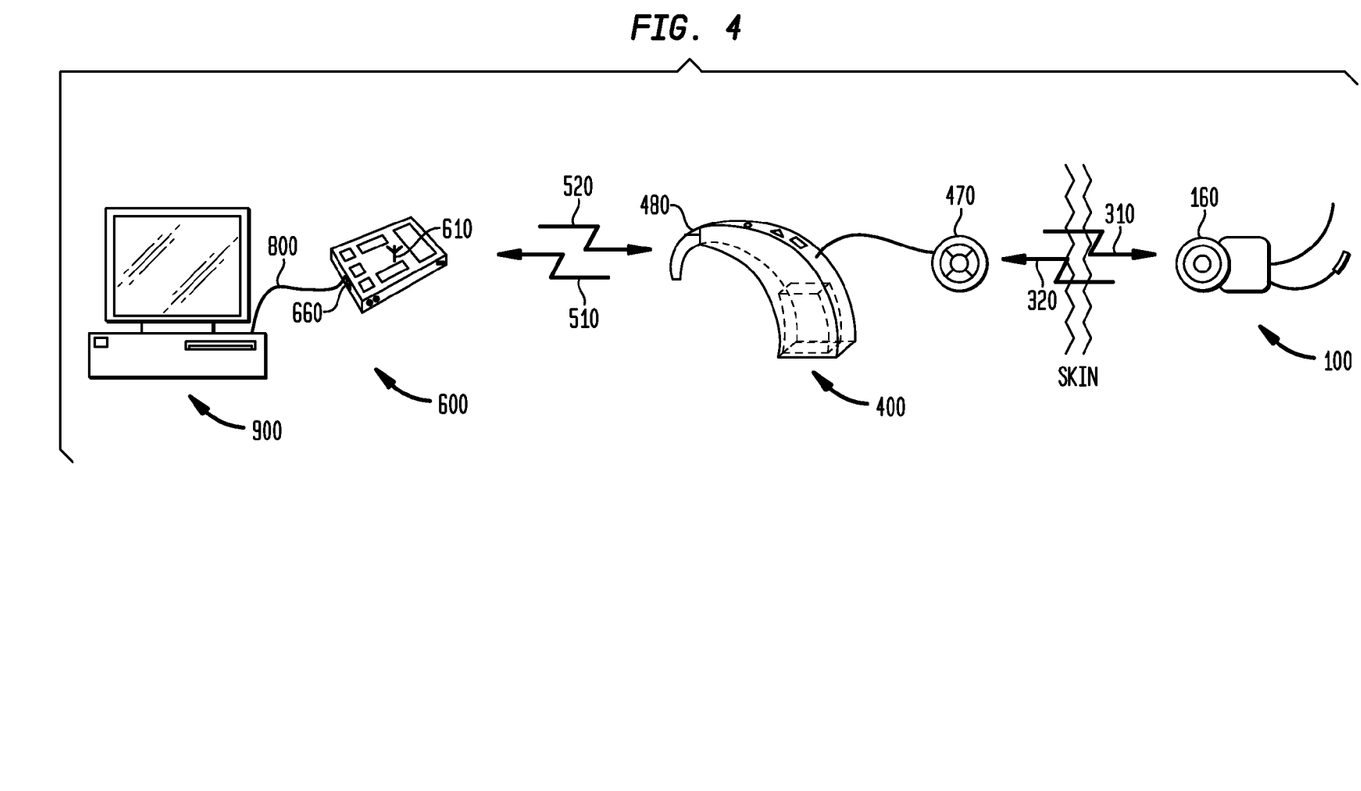
FIG. 4 is a perspective view of a partially implantable hearing aid system comprising a remote unit with a digital interface for e.g. wired connection to a PC and a RF wireless interface for communication with a second device, being a BTE device.

Remote unit 600 may also comprise an external digital interface port 660, such as a USB interface, connectable with a cable 800 to a personal home computer 900 or hand-palm computer (FIG. 4). This enables downloads or uploads of data between PC and BTE, PC and remote unit or PC and implant for changing firmware, software, maps or parameters. The additional advantage of interface port 660 is that the user of the system is able to do this at home with the same remote device if and when desired.

BTE device 400 is configured to select a frequency channel for the link 510, 520 from a predefined series of different frequency channels. The frequency channel the BTE may select, may be an interference free channel or the least interfered channel from the predefined series. The choice of which frequency channel to select for the wireless link 510, 520 is preferably a decision made solely by BTE device 400. The selected frequency channel will be the only frequency channel on which the BTE device "listens" to another device, such as a remote unit 600 at a given instant of time. BTE device 400 is configured to respond to the other device (e.g. remote unit 600) on the selected frequency channel.

BTE device 400 may choose to change its selection and to select another frequency channel from the series, e.g. when the frequency channel becomes highly interfered. BTE device 400 may be arranged to select the least interfered frequency channel. Hence, the selected frequency channel is not a fixed frequency channel.

Remote unit 600 does not a priori contain information regarding which frequency channel BTE device 400 has selected for wireless link 510, 520. Therefore, remote unit 600 may be configured to use different frequency channels for wireless link 510, 520. Those different frequency channels may be the same predefined series of frequency channels from BTE device 400.

Figure 7:
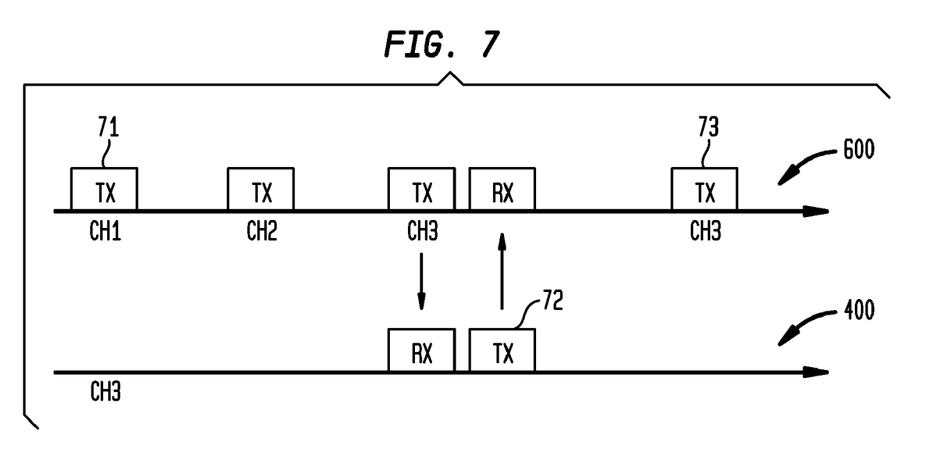
FIG. 7 is a schematic view of a transmission protocol for wireless communication according to one embodiment of the present invention.

Remote unit 600 is configured to transmit commands to BTE device 400 over wireless link 520. As remote unit 600 does not a priori contain information regarding which frequency channel BTE device 400 is currently listening, the following protocol is set up for the transmission of a command from remote unit 600 to BTE device 400, in accordance with one embodiment of the present invention. This embodiment of the protocol is illustrated in FIG. 7.

Remote unit 600 transmits a command 71 over link 520 using a first (physical) frequency channel CH1. Thereafter, remote unit 600 awaits for predefined time whether a reply signal is received. If CH1 is not the frequency channel on which BTE device 400 is currently listening, remote unit 600 will not receive a reply signal on CH1, and selects a second frequency channel CH2. The same command 71 is transmitted over second frequency channel CH2. Remote unit 600 awaits during the predefined time whether a reply signal is received. If no reply signal is received, remote unit 600 selects a third frequency channel CH3 and transmits the same command 71 over the third frequency channel. Assuming that CH3 is the frequency channel selected by BTE device 400 at that time, then BTE device 400 will receive the command 71 transmitted over channel CH3. BTE device 400 then transmits a reply signal 72 over the same frequency channel CH3 over link 510, the reply signal being received by the remote unit 600. Upon reception of reply signal 72, remote unit 600 contains information indicating that CH3 is the frequency channel that is currently selected by BTE device 400.

For the transmission of a next command 73, remote unit 600 uses physical frequency channel CH3 as a preferred frequency channel for initial transmission. Hence, frequency channel CH3 will be the first channel over which remote unit 600 transmits command 73. Should BTE device 400 in the meantime have changed the frequency channel, then remote unit 600 follows the same protocol as above for transmission of the command. Hence, if after a predefined wait time no reply signal is received on CH3 for command 73, another frequency channel is selected by the remote unit (e.g. CH1) and command 73 is transmitted over that frequency channel and so on.

Hence, in the protocol described above, remote unit 600 may be considered a master for commands and BTE device 400 a slave for commands. BTE device 400 is however a master for the selection of frequency channels and remote unit 600 is a slave for the selection of frequency channels.

In another embodiment, remote unit 600 may be arranged to transmit a command 71 multiple times over a same frequency channel CH1 before switching to a second frequency channel CH2.

The transmission protocol for wireless link 510, 520 allows for the saving of power by BTE device 400. The receiver (and transmitter) unit of BTE device 400 for link 510, 520 may remain idle as long as no command is received on the selected frequency channel (e.g. CH3 in FIG. 7). Moreover, the transmission of data over link 510, 520 may be arranged as a burst transmission at very high symbol rate or bit rate. A burst transmission at high bit rate allows to lower the duty cycle of the RF transmissions.

The data transmitted over communication link 510, 520 may be digitally modulated. In digital modulation, an analog carrier signal is modulated by a digital bit stream. Digital modulation methods that may be implemented in embodiments of the present invention include but are not limited to phase shift keying, frequency shift keying, amplitude shift keying, minimum shift keying, on/off keying, orthogonal frequency division multiplexing and quadrature amplitude modulation.

Applying the kind of link described above for bidirectional wireless communication between BTE device 400 and remote unit 600 reduces overall system energy consumption, even for higher bit rate transfers. Additionally, energy consumption is reduced by the limited total transmission time of burst transmissions. Burst transmissions are transmissions that combine a very high data signalling (symbol) rate with very short transmission times. Each burst hence has a limited duration. In between different bursts, the transmitter may be idle and draw only a fraction of the power drawn when transmitting the bursts. Typical total transmission times of burst transmissions according to the invention may fall in the range between 0.1% and 50%. Burst transmissions are digitally modulated transmissions.

The use of the above transmission protocol is not limited to communications between a BTE device and a remote unit, but may also be implemented, for example, for the communication between a BTE device 400 and a cochlear implant 100.

Figure 5A:
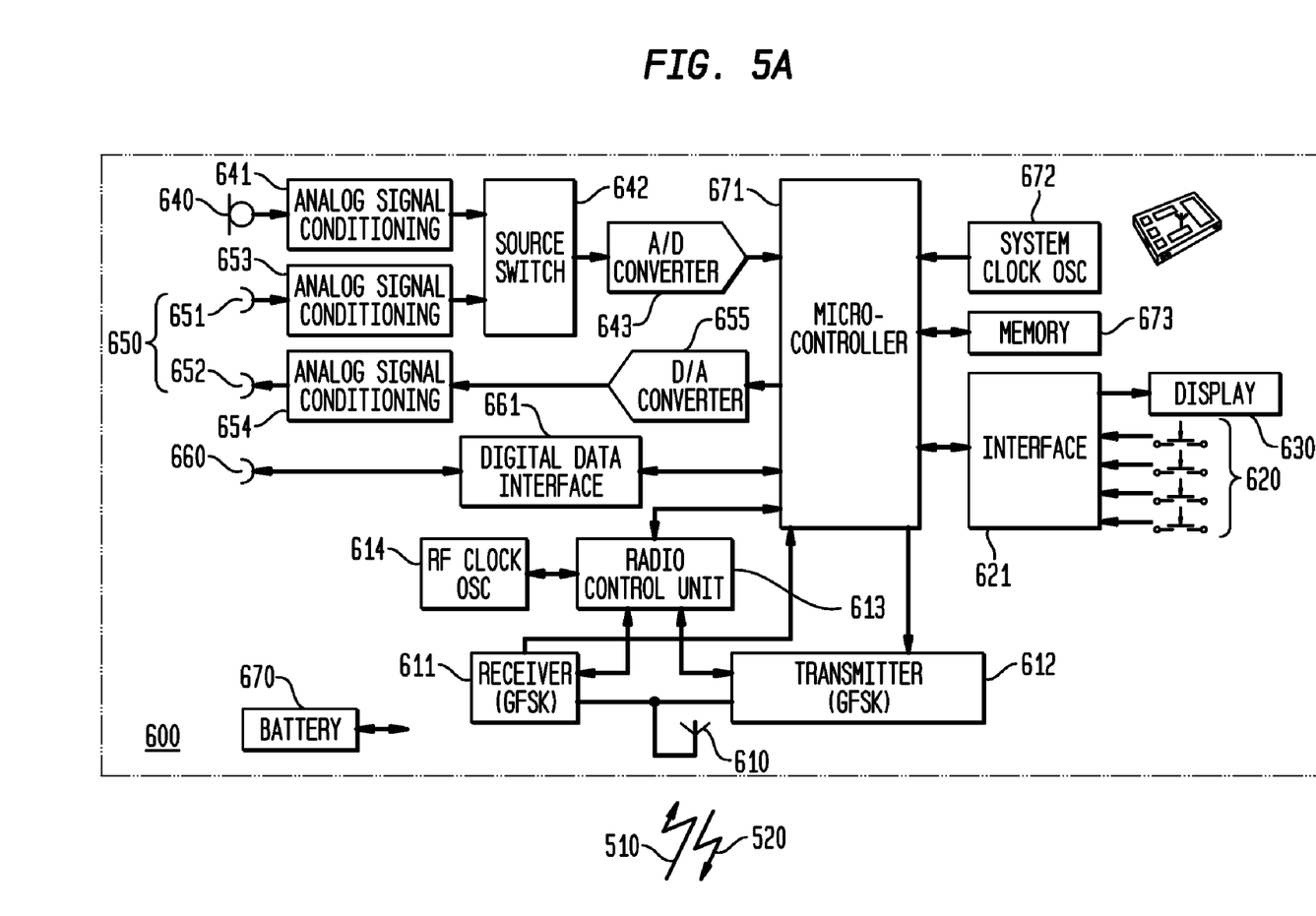
FIG. 5A and FIG. 5B are block diagrams of embodiments of a remote unit and a BTE device, respectively, each comprising means for operating a wireless burst transmission link in accordance with one embodiment of the present invention.
Figure 5B:
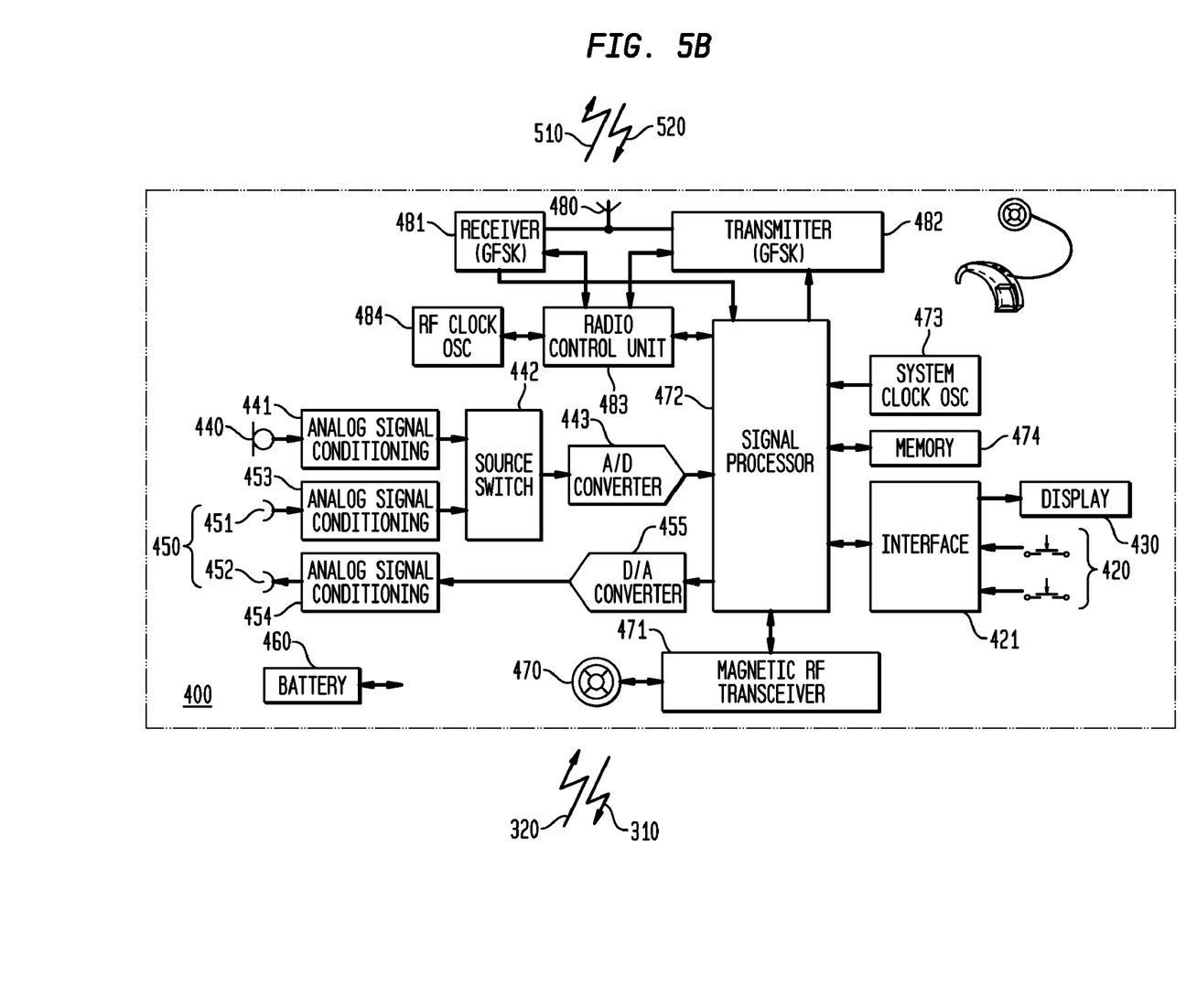

In the embodiment illustrated in FIGS. 5A and 5B, BTE device 400 and remote unit 600 are provided with the capability to operate the wireless communication link 510, 520 as a digitally modulated, high bit rate burst transmission link. Remote unit 600 may draw energy from a replaceable battery system 670 and comprises a centralized microcontroller 671 with limited persistent and non-persistent memory 672, a system clock 672, digital interfaces 621 and 661, analog interfaces 641, 653 and 654, an analog source switch 642, a digital to analog converter 655, an analog to digital converter 643 and a digital modulated RF transmitter 612 and RF receiver 611 block. The analog interfaces are represented in FIGS. 5A and 5B as signal conditioning blocks, including level shifters, analogue amplifiers, attenuators and filters.

A radio control unit 613 controls the timing and synchronisation over the incoming and outgoing data packets of the wireless RF link. An accurate clock source 614 provides the transmitter and receiver with a stable communication channel with predefined timing slots for RF burst transmissions and receptions. Those transmissions and receptions comprise telemetry signals such as control data, command data, program data and signalling data. Furthermore, radio control unit 613 may be configured to change the frequency channel of transmission of a command through transmitter 612 and antenna 610. Clock source 614 may be used for generating accurate frequencies for the wireless link.

The centralized microcontroller is configured to translate the incoming analog and digital interface and control signals 620 to a format adapted to transmitter 612. Furthermore, it is configured to interpret and adapt the incoming data from receiver 611 and to transfer it to the respective outgoing interfaces such as a display 630, a digital data interface output or analog output 652. In order to further reduce energy consumption, the microcontroller works on a system clock 672 at low speed when idle or in sleep mode.

BTE device 400 of FIG. 5B operates on a replaceable battery system plugged into compartment 460 and comprises a high intelligent signal processor 472 with sufficient persistent and non-persistent memory 474, a system clock 473, a digital interface 421, analog interfaces 441, 453, 454, an analog source switch 442, a digital to analog converter 455, an analog to digital converter 443 and a digital modulated RF transmitter 482 and RF receiver 481 block. The analog interfaces are represented as signal conditioning blocks, including level shifters, analog amplifiers, attenuators and filters.

Analogously to remote unit 600, a radio control unit 483 in BTE device 400 controls the timing and synchronisation over the incoming and outgoing data packets of the wireless RF link. An accurate clock source 484 provides the transmitter and receiver with a stable communication channel with predefined timing slots for RF burst transmissions and receptions. Those transmissions and receptions may comprise telemetry signals such as control data, command data, program data and signalling data. Radio control unit 483 is arranged to select a frequency channel from a predefined series of frequency channels for communication over wireless link 510 and 520. Clock source 484 may be used for generating accurate frequencies for the wireless link.

The receiver, transmitter and radio control unit of BTE device 400 and/or remote unit 600 may be implemented on a single ASIC (application specific integrated circuit).

BTE device 400 primarily processes (meaning filtering, encoding, converting etc.) the airborne auditory signals captured from local microphone 440 or analogue interfaces, or remote microphone 640 or analog interfaces. The converted signals are transferred via a transcutaneous magnetic link to implant 100 using a magnetic transceiver 471 and antenna coil 470. BTE device 400 may comprise a sound processor unit.

Furthermore, BTE device 400 is also arranged to process the incoming data from the transcutaneous magnetic link transceiver 471 and receiver 481. Depending on predefined events or timings, BTE device 400 may transfer relevant data to the local digital interface 421, display 430 or to the RF transmitter 482.

Figure 6:
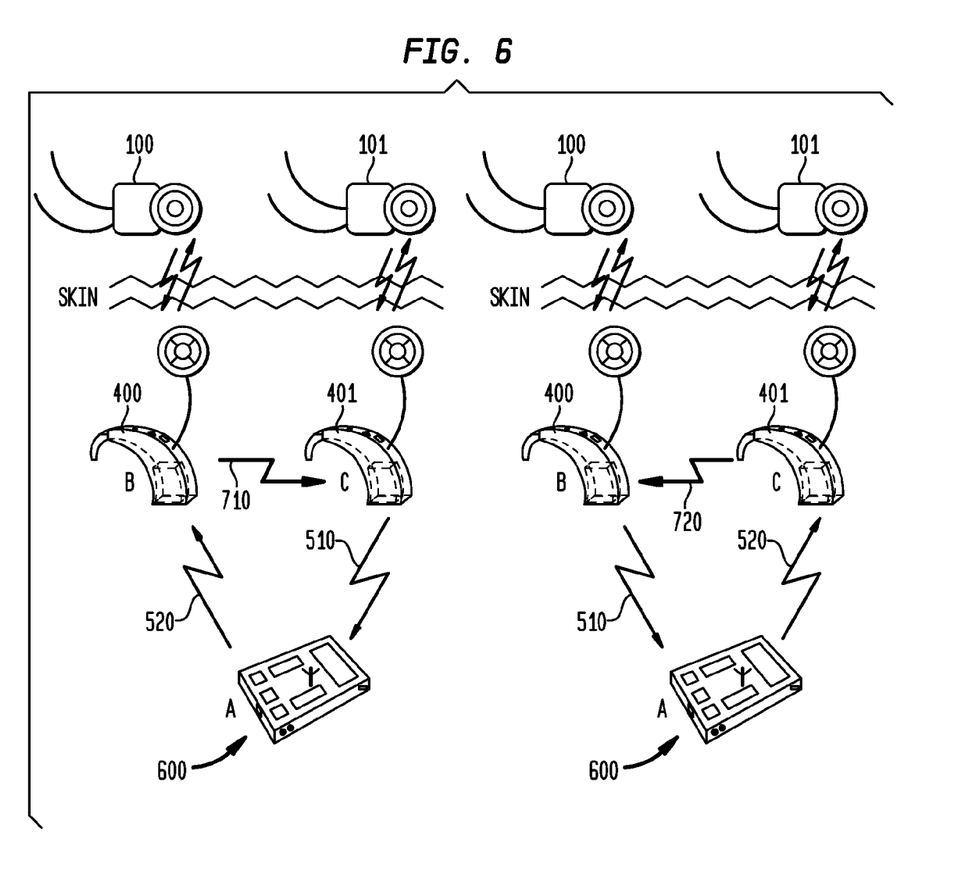
FIG. 6 is a perspective view of a communication arrangement within a partially implantable hearing aid system comprising a remote unit, two BTE devices, and two cochlear implants, in accordance with one embodiment of the present invention.

When a recipient is hearing impaired in both ears and has at least two hearing aid devices, one for each ear, the present invention provides a method of reducing the energy consumption of the total system. FIG. 6 is a perspective view of an embodiment of a method of transferring telemetry signals over a RF wireless communication link for a bilateral hearing aid system, which optimizes the overall system energy consumption. In the present embodiment, the recipient has two cochlear implants 100 and 101 implanted with corresponding BTE devices 400 and 401 respectively. The two hearing aid devices (BTE devices with cochlear implants) are controlled by a remote unit 600. Remote unit 600 is referred to as device 'A', a first behind-the-ear device 400 and second behind-the-ear device 401, are referred to as device 'B' and device 'C' respectively.

The scheme depicted on the left-hand side of FIG. 6 shows a remote unit A initiating a link. It sends a forward telemetry signal unidirectionally to device B via link 520. Link 520 may be operated according to the protocol as illustrated in FIG. 7. Device B may send a reply signal upon reception of the telemetry signal in order to acknowledge that the signal has been received. Device B may also not send that reply signal. Subsequently, device B sends this telemetry signal unidirectionally, unmodified or modified in a predetermined manner to device C via link 710. Devices B and C may operate on the same frequency channel for link 710 in order to limit the number of bursts. Link 710 may operate over a fixed frequency channel, or over different frequency channels. Next, device C sends this telemetry signal unidirectionally, unmodified or modified in a predetermined manner to the remote unit A via link 510. The signal that device C sends to device A may serve in one embodiment as a reply signal 72. It may be sent over a same frequency channel as the initial telemetry signal over link 520. The remote unit A, as initiator, internally validates the backward telemetry signal of device C with its forward telemetry signal for acknowledgement that data is uncorrupted and was accepted by devices B and C. If such a backward telemetry signal is not received by device A in due time, device A may select another frequency channel for link 520 and send the forward telemetry signal again.

An advantage of the above method of communication with three devices is that for sending a command from A to the other two devices B and C and for receiving an acknowledgement only three packets may be needed, whereas in case of mere direct communication with both devices A-B and A-C four packets would be needed for achieving the same. The amount of transmitted data is hence reduced and so is also the energy consumption. Moreover, the communication from device B to device C may additionally be used to transmit bilateral information.

The drawing on the right-hand side of FIG. 6 depicts an inversed situation, where a forward telemetry signal is first sent from remote unit A to BTE device C, then from BTE device C to BTE device B and finally from BTE device B to remote unit A. The hearing aid system comprising cochlear implants 100 and 101, BTE devices 400 and 401 and remote unit 600 may be arranged to operate according to only one or both schemes of FIG. 6. RF communication links 510, 520, 710 and 720 may operate according to the burst transmission scheme noted elsewhere herein.

Figure 2:
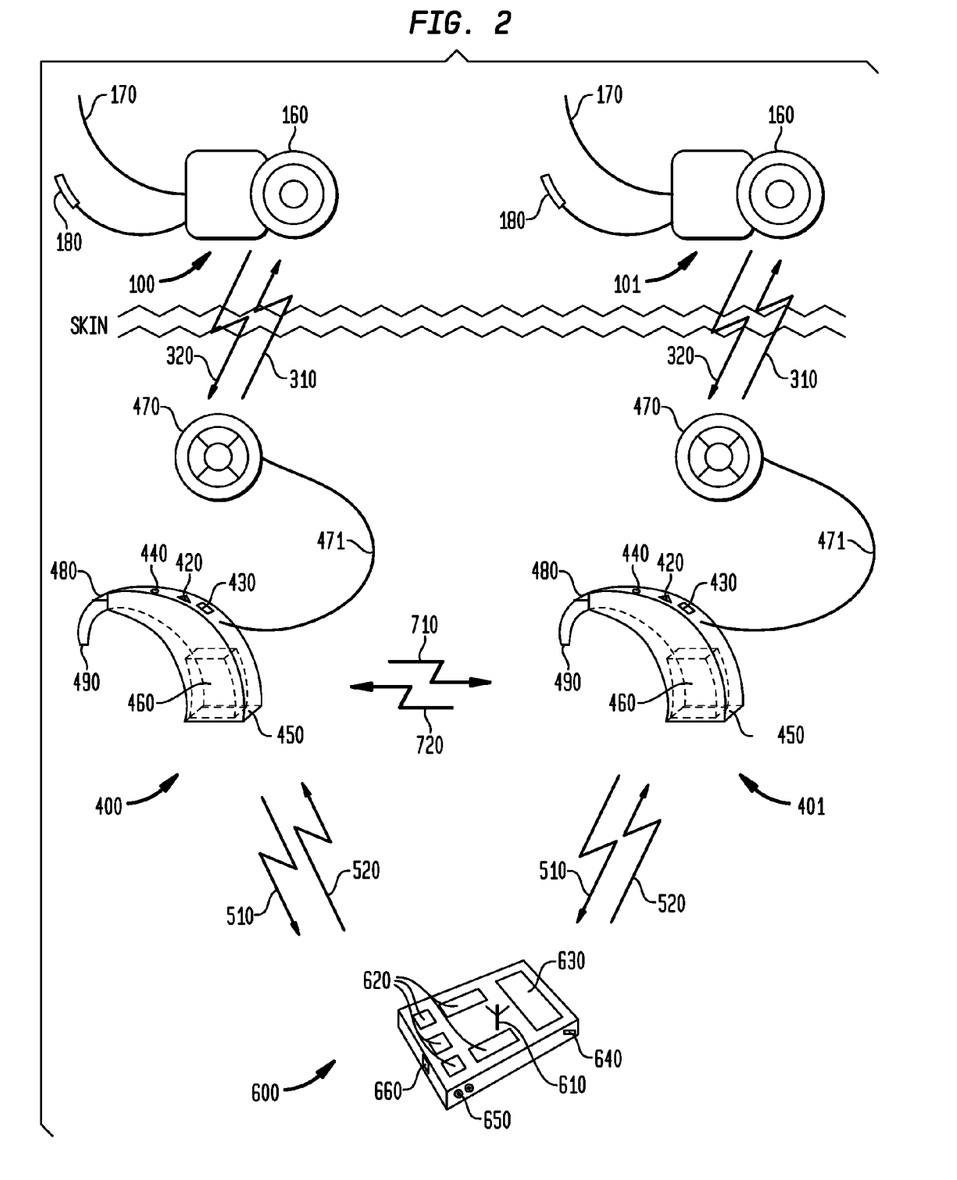
FIG. 2 is a perspective view of a partially implantable hearing aid system comprising two implantable devices (cochlear implants) and two BTE devices, in accordance with one embodiment of the present invention.

The advantage of the schemes of FIG. 6 lies in the fact that, instead of sending a message to each BTE device separately and waiting for both to acknowledge separately, as shown in FIG. 2, only one message is sent and received by the remote unit. This saves energy since only one transmission and reception timeslot is used, or transmitter and receiver circuitry power-on times are reduced.

What is claimed is:

1. A hearing prosthesis comprising a first device and a second device arranged for receiving commands from said first device, wherein:
    said first and the second devices each comprise a transmitter and receiver system configured for communication over a wireless communications link;
    said second device is configured to select a frequency channel for bidirectional wireless communication from a predefined series of frequency channels;

said first device is configured to transmit a command signal repeatedly over a plurality of frequency channels comprising the frequency channel selected by said second device; and said first device is further configured to initiate transmission of a subsequent command over said frequency channel selected by said second device.

2. The hearing prosthesis of claim 1, wherein said second device is further configured to transmit a reply signal over said frequency channel selected by said second device.

3. The hearing prosthesis of claim 1, wherein said receiver system of said second device is configured to be idle between two consecutively received commands.

4. The hearing prosthesis according to claim 1, wherein said wireless link is an electromagnetic RF link.

5. The hearing prosthesis of claim 1, wherein said wireless link is a magnetic induction RF link.

6. The hearing prosthesis of claim 1, wherein said communication over said wireless link is arranged in packets or bursts at a symbol rate greater than or equal to 100K symbols per second.

7. The hearing prosthesis of claim 1, wherein said first device further comprises a digital modulator coupled to said transmitter system of said first device and a digital demodulator coupled to said receiver system of said first device, and wherein said second device further comprises a digital modulator coupled to said transmitter system of said second device and a digital demodulator coupled to said receiver system of said second device.

8. The hearing prosthesis of claim 1, wherein said second device is configured to select the least interfered frequency channel of the predefined series of frequency channels for bidirectional wireless communication.

9. The hearing prosthesis of claim 1, wherein said transmitter and said receiver of said first and second devices are embodied in a CMOS integrated circuit.

10. The hearing prosthesis of claim 1, wherein said first device is a remote control unit comprising a human interface.

11. The hearing prosthesis of claim 1, wherein said second device is a behind-the-ear device.

12. The hearing prosthesis of claim 1, comprising a third device configured to communicate with said second device and said first device over a wireless link, wherein said third device is further configured to be carried by the same recipient of said second device and wherein said second and said third devices are each configured for wireless communication with each other.

13. A method of wireless communication between a first device and a second device of a hearing prosthesis, comprising:

selecting, by said second device, a frequency channel for bidirectional wireless communication from a predefined series of frequency channels;

sending a command from said first device repeatedly over a plurality of frequency channels comprising the frequency channel selected by said second device, until a reply signal is received by said first device; and using said frequency channel selected by said second device as one of a few initial frequency channels to transmit a subsequent command to said second device.

14. The method of claim 13, wherein sending a command comprises:

selecting a first frequency channel;

transmitting the command over the first frequency channel and waiting during a first idle time for a reply signal from the second device; and repeating the selecting and transmitting steps for a second frequency channel if no reply signal is received during said first idle time or halting said selecting and transmitting steps upon reception of the reply signal.

15. The method of claim 14, wherein said transmitting the command comprises:

transmitting said command repeatedly for a predefined number of times over a same frequency channel.

16. The method of claim 14, wherein said transmitting said command comprises transmitting said command as one or more RF bursts.

17. The method of claim 16, wherein said one or more bursts are transmitted at a symbol rate higher than or equal to 100K symbols per second.

18. The method of claim 13, further comprising:

transmitting, by said second device, a reply signal upon reception of said command.

19. The method of claim 13, wherein said transmitting said command comprising:

encoding said command by a digital modulation scheme.

20. The method of claim 19, wherein said digital modulation scheme is based on phase shift keying, frequency shift keying, amplitude shift keying, minimum shift keying, on/off keying, orthogonal frequency division multiplexing, or quadrature amplitude modulation.

21. A method of wireless communication between multiple devices of a hearing prosthesis, the hearing prosthesis comprising a first device, a second device and a third device, wherein the method comprising:

transmitting a signal from the first device to the second device;

receiving the signal by the second device, optionally modifying the signal in a predetermined manner and transmitting the signal, unmodified or modified in a predetermined manner, from the second device to the third device;

receiving the signal by the third device, optionally modifying the signal in a predetermined manner and transmitting the signal, unmodified or modified in a predetermined manner, from the third device to the first device and receiving the signal by the first device and comparing the signal that is received with the signal that was transmitted.

22. The method of claim 21, wherein said second and said third devices behind-the-ear device and the first device is a remote unit for controlling and programming the second and the third devices.

* * * * *